United States Patent [19]
Christou et al.

[11] Patent Number: 5,989,915
[45] Date of Patent: *Nov. 23, 1999

[54] PLANT TRANSFORMATION WITH EARLY IDENTIFICATION OF GERM LINE TRANSFORMATION EVENTS

[75] Inventors: Paul Christou, Madison; Dennis E. McCabe, Middleton, both of Wis.

[73] Assignee: Monsanto Company, St. Louis, Mo.

[ * ] Notice: This patent is subject to a terminal disclaimer.

[21] Appl. No.: 09/185,174

[22] Filed: Nov. 3, 1998

Related U.S. Application Data

[63] Continuation of application No. 08/627,195, Apr. 3, 1996, Pat. No. 5,830,728, which is a continuation of application No. 08/161,685, Dec. 2, 1993, Pat. No. 5,503,998, which is a continuation of application No. 07/485,111, Feb. 26, 1990, abandoned.

[51] Int. Cl.$^6$ ........................... C12N 15/00; C12N 15/29; C12N 15/82; A01H 4/00
[52] U.S. Cl. ........................... 435/468; 435/419; 800/278; 800/279; 800/287; 800/293
[58] Field of Search ................................. 435/468, 419; 800/278, 279, 287, 293

[56] References Cited

U.S. PATENT DOCUMENTS 5,830,728  11/1998  Christou et al. ..................... 435/172.3

*Primary Examiner*—Lynette R. F. Smith
*Assistant Examiner*—Thomas Haas
*Attorney, Agent, or Firm*—Nicholas J. Seay

[57] ABSTRACT

A method is disclosed for making more efficient the particle-mediated germ line genetic transformation of bean species such as soybean. After a particle-mediated transformation event, in the absence of a selectable marker gene, relatively large numbers of plants must be regenerated to find the relatively low likelihood germ line transformation events which have occurred. It has been discovered that using in the transformation process a marker gene linked to the gene of interest, and by excising a segment of the stem of the shoot during the regeneration process and assaying the segment for the marker gene, certain patterns or phenotypes can be identified in the stem segment which are associated with an increased frequency of germ line transformation events. As the plants are regenerated, other indices of gene expression, at the first trifoliate leaf stage and at the third or fourth trifoliate leaf stage, also serve as markers of the likelihood of germ line transformation. By using these markers in the relatively early stages of plant regeneration to assay for likelihood of germ line events, it is possible to concentrate regeneration efforts on plants most likely to yield germ line events, and to discard the others, so as to lower the burden and effort in achieving a desired number of transformation events.

1 Claim, 2 Drawing Sheets

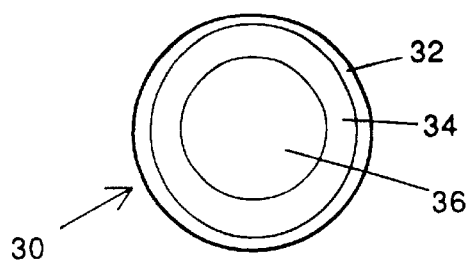
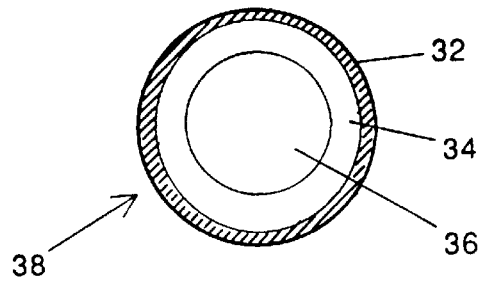
FIG. 3  FIG. 4
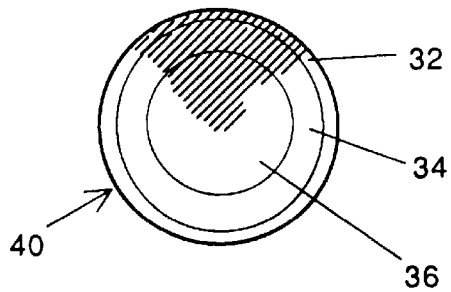
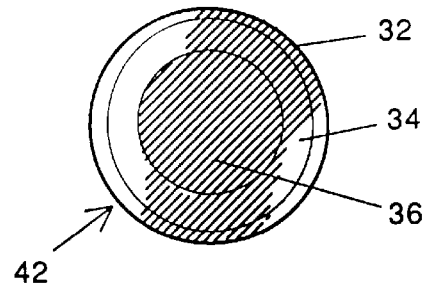
FIG. 5  FIG. 6
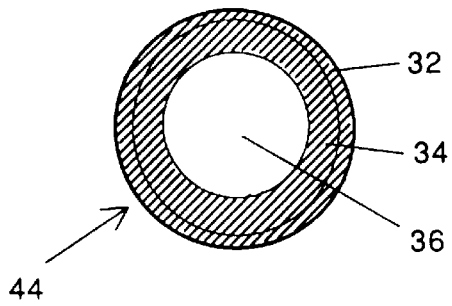
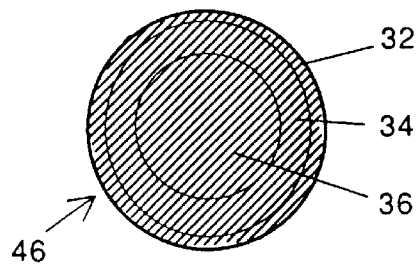
FIG. 7  FIG. 8

PLANT TRANSFORMATION WITH EARLY IDENTIFICATION OF GERM LINE TRANSFORMATION EVENTS

CROSS REFERENCE TO RELATED APPLICATION

This application is a continuation of application Ser. No. 08/627,195, filed Apr. 3, 1996, now U.S. Pat. No. 5,830,728, which was a continuation of application Ser. No. 08/161,685, filed Dec. 2, 1993, now U.S. Pat. No. 5,503,998, which was a continuation of application Ser. No. 07/485,111 filed Feb. 26, 1990, now abandoned.

FIELD OF THE INVENTION

The present invention relates to the genetic transformation of plants in general, and relates, in particular, to the efficient germ line transformation of soybean plants utilizing particle-mediated techniques for plant transformation.

BACKGROUND OF THE INVENTION

It is now becoming possible to introduce into some of the major crop plants foreign genes of potential interest in those plants. This process of genetic engineering has been accomplished with certain model species, such as tobacco, petunia, and carrot, and has now been accomplished in such major crops species soybean and cotton. In procedures for the genetic engineering of plants, it is desired that the genetic transformation of the plant tissues be of the germ line of the plant tissues. Germ line refers to the inheritable genetic material of the plant which is permanently altered by the transformation process in such a fashion that the plant will pass to its progeny by normal genetic inheritance the inserted foreign gene. While the transformation of somatic, or non-germ line cells, may be desired in some instances, in general in the genetic engineering of crop plants it is desired that germ line transformation of plant lines be achieved as quickly and efficiently as possible.

The most common previously utilized technique for the genetic engineering of plants involves the use of the soil-dwelling plant pathogenic bacterium *Agrobacterium tumefaciens*. *A. tumefaciens* has the natural ability to transfer a portion of its DNA, referred to as T-DNA, into the genome of susceptible plant cells. By changing the native T-DNA in an Agrobacterium strain, it is possible to use this unique trait of Agrobacterium to transfer desired genes into single plant cells. If the introduced gene includes a selectable marker, such as a herbicide or antibiotic resistance trait, it is possible thereafter to select for transformed cells in a tissue culture by imposing the putative transformant tissues to the selection pressure of the appropriate antibiotic or herbicide. Unfortunately, in soybean almost all cultivars are resistant to Agrobacterium infection and are thus very resistant to transformation with Agrobacterium. In addition, antibiotic resistant markers, such as kanamycin resistance commonly used in Agrobacterium plant transformation procedures with other plant species, have been found to be of limited utility in soybean transformation experiments. Accordingly, while it may be possible to utilize Agrobacterium-mediated transformation techniques in soybean, it is a difficult endeavor because of the lack of effective selectable markers.

Other techniques for transforming plants do exist, however. In particular, there exists a general approach to the transformation of plant cells which is based on delivering the transforming DNA into the plant cells by coating the DNA onto small inert carrier particles which are physically hurled into the target plant tissues. The technique of particle-mediated plant cell transformation was first demonstrated with somatic cells in such tissues as the epidermal tissue of onion and other such model cell cultures. Klein et al., *Nature*, 327:70–73 (1987). Later the originators of the particle-mediated transformation technique were able to achieve genetically engineered tobacco plants by the transformation of tobacco in tissue culture, using a selectable marker, which was then subsequently regenerated into whole plants. Klein et al., *Proc. Natl. Acad. Sci. USA*, 85:8502–8505 (1988). Rather than attempting to use particle-mediated transformation techniques on plant cells in culture, another approach was developed in which the growing meristems of plants were subjected to a particle-mediated transformation event. From such a technique, stable transformation of the germ line of soybean plants was achieved. McCabe et al., *Bio/Technology*, 6:923–926 (1988). This technique is not dependent on the availability of a selectable marker for the plant species.

In developing the technique for the germ line transformation of soybean plants using a particle-mediated technique based on meristem transformation, it was discovered that the transformation events often resulted in chimeric plants, which are plants in which some, but not all, of the tissues had been genetically transformed with the introduced DNA. McCabe et al., supra. Although the technique was thus useful to create genetically engineered plants, it was somewhat burdensome in the sense that large numbers of tissues had to be subject to transformation events, and large numbers of plants had to be cultivated from the putative transformed tissues in order to discover those particular shoots and plants which properly expressed the introduced DNA. Therefore, the ability to identify transformation events early in the process giving rise to heritable germ line transformation of tissues creates the ability to effectuate dramatic savings in the practical and cost-effective genetic transformation of plants resulting in reduced labor costs and reduced time and energy expended in cultivating the non-transformed tissues which were subject to the transformation events.

In seeking a germ line transformation of a plant species, such as soybean, it would be helpful if the progenitor tissue of the germ cells of the plant were identified in the growing meristem or shoot. Unfortunately, the science of developmental morphology of plant cells has not developed to the point that the ancestor cells of the soybean germ cells is known. Accordingly, if it is a plant meristem or embryo that is being transformed, no present knowledge exists as to which precise cells in that meristem or embryo must be transformed to achieve germ line transformation. Therefore, any correlation between categories of cells transformed in a growing soybean plant and a germ line transformation event would have to be determined empirically.

SUMMARY OF THE INVENTION

The present invention is summarized in that a process for creating and identifying germ line transformed soybean plants is provided in which a number of growing meristems of soybean plants are subject to a particle-mediated transformation procedure and that the resulting tissues are subject to a series of early-stage tests of phenotypic markers in primary transformant tissues to search for phenotypic markers which have a high correlation to germ line transformation events, so that only the marked tissues will be subject to the investment of energy in regenerating whole plants therefrom.

It is an object of the present invention to provide a method of particle-mediated transformation of plants which is inherently more efficient and cost-effective than previously available techniques.

It is an object of the present invention to make more cost effective the genetic engineering of plants, and soybean plants in particular, by identifying, at the earliest stage possible in the process, those plants which are most likely to yield germ line transformants so that only those plants need to be cultivated into mature plants.

It is another object of the present invention to optimize the use of reporter or marker genes in plant transformation experiments even in the absence of selectable markers to make possible the genetic engineering of plants in those plants for which reliable dominant selectable markers are not available.

Other objects, advantages, and features of the present invention will become apparent from the following specification when taken in conjunction with the accompanying drawings.

BRIEF DESCRIPTION OF THE DRAWINGS

FIG. 3 is a highly stylized illustration of a cross-section through a soybean stem.

FIGS. 4–8 are other stylized illustrations of a cross-section through a soybean stem showing various phenotype of marker gene expression.

DESCRIPTION OF THE INVENTION

Figure 1:
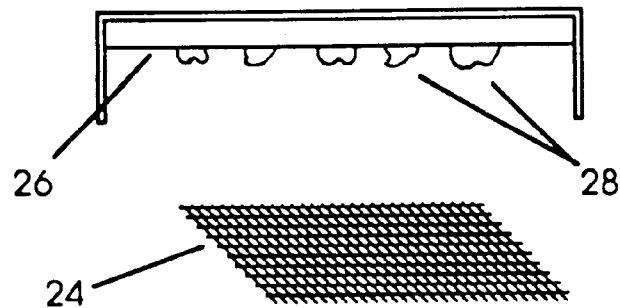
FIG. 1 is a schematic illustration of an apparatus suitable for use in the particle-mediated transformation of plant tissues.

In accordance with the method of the present invention, a series of indices are described which are used to identify high likelihood germ line transformation events among the shoots and plants produced from a particle-mediated plant transformation process. These indices are based on a classification of certain phenotypes of expression of a marker gene in tissues of a regenerating plant at certain defined stages.

To fully understand the advantages of the present method, it is helpful to appreciate certain considerations about the nature of accelerated particle-mediated transformation of plants. Since the transforming DNA is carried into the plant tissues on particles, and since the number of particles must be limited to avoid destroying the plant tissues transformed, only a percentage of the cells in a treated plant tissue will receive transforming DNA, and only a percentage of those cells will be transformed. Therefore, in the absence of a selection agent to kill non-transformed cells preferentially, the result of regenerating plants from such treated tissues will be plants most of the tissues of which are not transformed. It has been found that even of the plants which are at least in part transformed, most of the transformations do not result in germ line transformations. This invention is therefore directed to identifying those desired germ line transformation events at an early stage so that regeneration of the non-germ line plants can be minimized.

Thus it is not necessary to use the early germ line identification process described here to achieve a germ line transformation of soybean. It is possible to regenerate all plants recovered from the treated tissue, sexually propagate all the plants and assay all the progeny. The drawback to this approach is that most of the effort in the regeneration and propagation process will be wasted on non-germ line transformation events. The present invention helps to avoid that waste and thereby assist in the efficient creation of lines of genetically transformed soybean.

The present invention is thus based on a technique involving the particle-mediated transformation of plant cells. Therefore, to better understand the context of the present invention, it is necessary to understand the general technique of particle-mediated transformation of plant cells and the apparatus which may be used therefore.

In the process of particle-mediated transformation of plant cells, a carrier particle consisting of a small inert relatively dense particle of material is coated with a transforming genetic construction of DNA and then is physically accelerated so that it is delivered into the interior of the growing meristematic or embryonic cells to be transformed. The transforming DNA is thus carried into individual cells, but the carrier particles are small enough such that the individual cells are neither destroyed nor seriously incapacitated. It has been found that by delivering DNA on such carrier particles in such a fashion into the cells of plants, such as soybeans, whole transformed germ line plants can be obtained to result in transgenic plants in plant lines.

There are several factors which are necessary to be considered in the creation of germ line plant transformations in these fashions. The genetic construction must be one properly constructed to be expressed in plant tissues. The apparatus utilized must be of a type capable of delivering the carrier particles with the coated DNA on them into plant cells in such a fashion that a suitable number of cells are transformed. There are many types of mechanical systems which can be envisioned to accelerate biologically inert small carrier particles. Possible mechanisms include ballistic explosive acceleration of particles, centrifugal acceleration of particles, electrostatic acceleration of particles, or any other analogous system capable of providing momentum and velocity to small inert particles. The mechanism used herein to achieve particle-mediated plant transformation is based on an adjustable electric voltage spark discharge device. The apparatus is illustrated in a schematic fashion in FIG. 1.

The particle-acceleration apparatus is generally indicated at 10 in FIG. 1. The apparatus consists of a spark discharge chamber 12 into which are inserted two electrodes 14 which are spaced apart by a distance of approximately one to two millimeters. The spark discharge chamber 12 is a horizontally extending rectangle having two openings 16 and 18 extending out its upward end. The opening 16 is covered by an access plate 20. The opening 18, located on the side of the rectangle of the spark discharge chamber 12 opposite from the electrodes 14, is intended to be covered by a carrier sheet 22. The electrodes 14 are connected to a suitable adjustable source of electric discharge voltage. Such a source of electric discharge voltage would preferably include suitable electric switching connected to a capacitor of the one to two microfarad size range, with the amount of the voltage of the charge introduced onto the capacitor being adjustable, such as through the use of an autotransformer, through a range of perhaps 1 to 50,000 volts. Suitable high voltage electric switching (not shown) is provided so that the capacitor can safely be discharged through the electrodes 14 so that the apparatus can be used conveniently by a user.

The carrier sheet 22 intended to be placed upon the opening 18 in the spark discharge chamber 12 is a planar sheet of relatively stiff material, such as a sheet of aluminized saran coated mylar. Above the opening 18 in the discharge chamber 12, positioned approximately 15 millimeters above it, is a retaining screen 24. Placed above the retaining screen 24 at a distance of approximately 5 to 25 millimeters above the retaining screen, is a target surface 26. The target surface 26 can be any suitable culture surface onto which the material to be transformed may readily be placed such as, most conveniently, an overturned petri dish into which the plant tissues have been positioned for culture. Copies of the exogenous foreign genetic construction intended to be transformed into the plant tissues are prepared by suitable DNA preparation techniques well known to those of ordinary skill in the art, and multiple copies of the genetic construction are made. The copies of the foreign genetic construction, in aqueous solution, are then coated onto small particles of a durable dense biologically inert carrier material, such as gold, the carrier particles typically being in a size range of 1 to 3 microns. The carrier particles with the exogenous genetic construction thereon are then placed upon the carrier sheet 22, which is inserted at the proper opening on the top of the spark discharge chamber 12. The target surface 26, including the living plant material thereon, is then placed in position above the retaining screen 24. A small droplet of water, preferably about 10 microliters in size, is then placed bridging between the ends of the electrodes 14. The access cover 20 is placed in position on top of the spark discharge chamber 12. At this point the entire apparatus is enclosed in a vacuum chamber and a vacuum is drawn until it is in the range of approximately 500 millimeters of mercury. As the vacuum is being drawn, a supply of helium is bled into the vacuum chamber, replacing the remaining atmosphere in the chamber with helium. The lower relative density of helium, combined with the reduced pressure, helps to lower the drag on the gold particles.

At this point, the spark discharge between the electrodes 14 may be initiated by the user. This is done by means of the appropriate electric switching which applies the voltage stored in the capacitor across the terminals of the electrodes 14. The force of this electric discharge bridges the spark discharge gap between the electrodes 14 instantly vaporizing the small droplet of water previously placed therebetween. The force of the vaporization of that water creates a shockwave within the spark discharge chamber 12 which radiates outward in all directions. The impact of the radiating shockwave upon the carrier sheet 22 propels the carrier sheet 22 upward with great velocity. The upwardly traveling carrier sheet 22 accelerates until it contacts the retaining screen 24. The use of the helium within the vacuum containment for the apparatus provides less drag on the flight of the carrier sheet 22 as well as the carrier particles. At the retaining screen 24, the carrier sheet 22 is retained, and the carrier particles coated with the exogenous genetic construction previously coated thereon fly off of the carrier sheet and travel freely onward toward the target tissues. The small carrier particles then proceed into the cells of the target tissues placed on the target surface 26, and pass freely into the cytosol of the cells placed thereon. The actual momentum of the carrier particles as they impact the surface of the target tissues is adjustable, based upon the voltage of the initial electric discharge applied to the electrodes 14. Thus, by varying the amount of the electric discharge applied across the electrodes 14, the velocity by which the particles impact the target can be adjusted, and thus the depth of penetration of the carrier particles into the tissue of the target tissues can be adjusted continuously throughout the range of adjustment provided for the electric voltage applied across the electrodes 14.

To be useful in a particle-mediated transformation technique, the transforming exogenous genetic construction must be capable of performing some useful function in the cells of target plant tissues. The transforming genetic construction, which will normally be a chimeric construction in the sense that its DNA originates from more than one organism, should be capable of expressing in the target tissues gene product such as a foreign protein of interest or an antisense RNA strand. Such foreign genetic constructions, usefully embodied in expression cassette vectors for use in plant cells, are known to those of ordinary skill in the art. Typically such plant expression cassette vectors includes, besides the coding sequence of the desired exogenous or foreign gene, appropriate flanking regulatory sequences suitable for expression of the foreign gene in the plant cells, such as a promoter sequence capable of initiating transcription and a translational terminator to terminate translation of a message if protein synthesis is desired. It has been previously demonstrated that typical promoters and transcription terminators found to be effective in other plant tissues are effective in soybean as well.

The transforming genetic construction may also include a marker gene. Such a marker gene need not be a selectable marker. It need only be a marker the presence of which can be assayed using a minimal amount of plant tissue, by appropriate biochemical or phenotypic trait which may be observed in transgenic plant tissues. Such a marker gene may be the transforming DNA itself, if a completely biochemical assay for the presence of the transforming DNA is used, such as a polymerase chain reaction type of assay for the DNA itself. One convenient type of marker gene capable of detection by a phenotypic assay is the GUS gene described by Jefferson et al., *Embo J.,* 6:3901–3907(1987). The GUS gene, coding for the enzyme beta-glucuronidase which can be expressed in plant cells and the expression of which, in a tissue-destructive assay, will turn a convenient substraight, indigo-glucuronide, or 5-bromo-4-chloro-3-indolyl glucuronide blue in color in an in situ assay in plant tissues. Thus, the use of the GUS gene provides a convenient colorimetric assay for the expression of introduced DNA by phenotypic analysis in transformant plant tissues. Thus, in a typical transformation procedure, the desired gene of interest would be coupled in tandem in a single genetic construction, a DNA strand, with a GUS gene, and then the detection of the transforming DNA in plant tissues would be done by phenotypic analysis for the expression of the GUS enzyme in the target plant tissues.

Several plant tissues of soybean may be genetically transformed by such a particle-mediated transformation technique using the apparatus of FIG. 1. It has been found most conveniently that the excised embryonic axes from immature or mature soybean seeds may be readily transformed utilizing the procedure. The embryonic axes are excised from the soybean seeds and the primary leaves are removed to expose the meristem of the embryo. The axes are then plated on target plates containing 1% water-agar. The plates are then used as a target surface in the apparatus of FIG. 1 for a particle-mediated transformation event. The axes may then be plated in the dark on MS basal medium as modified by Barwale et al., *Planta,* 167:473–481 (1986) for regenerating zygotic embryos. This particular medium contains a high level of benzylaminopurine which induces multiple shoot formation in the plated embryonic tissues. Following incubation for one to two weeks in the dark, the tissues are transferred to the same basal medium with lower concentrations of benzylaminopurine, and then are cultivated in the light to promote shoot elongation. Using this technique, multiple shoots will be derived from the primary and axillary meristems on the embryonic tissues. These shoots may then be grafted onto soybean roots, or induced to form roots, to regenerate whole intact and sexually mature soybean plants. It is these shoots, and the soybean plants regenerated therefrom, which are subject to the screening techniques described herein so as to result in high numbers of germ line transformant plants.

When the soybean shoots or plantlets resulting from tissues subject to a transformation process, such as has been described above, are regenerated into whole mature plants, it has been found that only a fraction of the resulting soybean plants will prove to be genetically transformed with the foreign DNA. The plants which are regenerated from the shoots resulting from this tissue are referred to as R0 plants, while their progeny in successive generations are referred to as R1 and R2, etc. In addition to having a low frequency of genetic transformation within the R0 plant generation, of the R0 plants which exhibit some genetic transformation, most of the plants will be chimeric. By the use of the term chimeric in this sense, it is intended to signify that the plants will be composed of tissues which are not genetically identical, i.e., the plants will have only a portion or fraction of their tissues transformed, while the remainder of the tissues are not genetically transformed. Since it is the object of the plant transformation process such as that described herein to create stably transformed plants which carry the foreign DNA in their germ plasm, and are capable of passing the inserted DNA into their progeny, it is necessary then to implement a screening procedure to ascertain how to recover the germ line transformation events from a number, and perhaps a large number, of putatively transformed R0 plants or plant tissues.

The method disclosed herein is intended to enable the screening of R0 shoots and plants from the putatively transformed plant culture to isolate those plants which will give rise to, or at least be most likely to give rise to, progeny plants which have had their germ line transformed. In this regard it should be noted that for the progeny grown from the R0 plants, that is to say from the R1 generation onward, if the progeny plants contained the inserted foreign DNA at all, they are clonal, that is to say, non-chimeric and have their germ line cells transformed. While events are observed in which the inserted DNA appears to be present in a clonal fashion in the R0 plant, but then is found completely absent in the R1 and R2 plants, if the gene is found to be present in the R1 plant, it will prove to be stably inheritable thereafter in those of the progeny of the R1 plant which inherit the inserted gene as a trait.

The present method is a screening technique rather than a selection technique. By that it is meant that the plants, or portions of the plants, are screened for the presence of certain marker characteristics, but are not subjected to a selection criteria such as would be achieved by antibiotic or herbicide resistance routines. In part the use of such a screening technique, as opposed to a selecting technique, is required due to the absence of reliable selectable marker gene effective in soybean tissues. The preferred marker gene, as mentioned, to be the object of the screening process, is the GUS gene. The GUS assay is, however, destructive of the plant tissues and thus cannot be performed in vivo. It must therefore be performed on a portion of the tissues recovered from the plants to be screened and the portion of the tissue selected must be one that balances the need to gain an accurate reflection of the prospects for germ line transformation on the particular plant with the need to maintain the vigor of the plant tissues involved so that the very events sought are not lost during the assay process.

The method of the present invention is based on the selection of certain strategically located portions of plant tissue from the R0 plants during the regeneration process. In particular, three indices of the state of transformation of the R0 plants are utilized. The first index is a section of stem segment from the R0 shoot collected from the shoot prior to rooting. The second index is a section of the leaf phenotype at the first trifoliate stage of development of the seedling. The third index is a petiole/mid-rib section of a trifoliate leaf in a more mature plant, at the third or fourth trifoliate leaf stage. By doing histochemical assays for the enzyme coded by the GUS gene in each of these three stages, it is possible to predict with a high degree of confidence the germ line transformation events which have occurred. In fact, it is possible at a relatively early stage in the procedure to discard most (as many as 90–99%) of the regenerating R0 shoots and plantlets to concentrate on the remaining shoots or plantlets which have a high probability of yielding germ line transformation events. While the discarding of many such shoots or plantlets may seem wasteful, and will almost certainly involve the discarding of occasional truly transformed plants, the amount of labor and time saved by not taking large numbers of non-transformed plants to seed is large in comparison to the time involved in creating additional transformation events. Thus the laborious part of the process, i.e., taking the putatively transformed plants to seed and growing and testing the progeny, can be reduced to a minimum by the screening methodology disclosed herein.

The first index analysis of the transformed plants occurs when regeneration of shoots commences from the originally transformed plant explant. As the regenerating soybean shoots reach a finite and defined size, typically approximately 2 centimeters in size, the shoots may be isolated from the original explant and prepared for propagation, either by grafting or by hormone treatment to induce root formation. However, at the time the shoots are separated from the original explant, it is convenient at that point to take a relatively small segment of the stem from the basal portion of the separated shoot, i.e., a segment size of perhaps 2 millimeters. The stem segment can then be fixed, and subjected to the GUS histochemical assay. The result is a cross-sectional view of the stem of the soybean plant which will exhibit a color, i.e., blue, in those portions of the tissues of the plant which have been transformed. Based on an analysis of those tissues, it is then possible to predict for those stems which exhibit some enzyme activity, those plants which are most likely to yield a germ line transformation event.

A classification scheme has been devised to categorize the results of the stem segment assay. The transgenic primary regenerates were designated "B" when the GUS enzyme assay revealed that the gene was expressing in all of the epidermis, the cortex, and the pith of the stem segments assayed. The regenerates were designated "C*" or "P*" when the expression of the GUS gene was confined to 100% of either the cortex or the pith respectively of the shoot segment which was assayed. The regenerating shoots were classified as "C" when at least half of the cortex expressed the enzyme, and "c" when less than 50% of the cortex showed activity. Similarly a classification of P or p indicates GUS activity in more or less than 50% of the pith of the stem. The shoots were scored as "e" when the activity of the GUS gene could only be seen in the epidermis of the shoot. Examples were also observed in which the codes were used to indicate localized activity in multiple areas, for example, a score of c/P* indicates that the shoot expressed the GUS marker gene in 100% of its pith tissue, but in less than 50% of its cortex tissue. A classification of E*/p indicates the expression of the enzyme in 100% of the epidermis but in less than 50% of the pith and none of the cortex of the transformant plant.

FIGS. 3–8 illustrate the classification scheme of the stem segments. FIG. 3 is a highly stylized drawing of an ideal soybean stem cross-section in which 30 indicates the whole stem, 32 indicates the epidermis, which is greatly exaggerated in width, 34 indicates the cortex and 36 indicates the pith. Shading in FIGS. 4 to 8 is intended to represent blue color in the GUS assay. FIG. 4 illustrates a stem 38 classified as "E" since only the epidermis is expressing the GUS gene. FIG. 5 illustrates a stem 40 which would be classified as "c/p" since less than 50% of cortex or pith are expressing. The stem 42 of FIG. 6 would be classified as "c/P*" since all the pith but less than 50% of the cortex was transformed. The stem 44 of FIG. 7 would be "C*". As should be apparent, the stem 46 of FIG. 8 represents a "B" stem segment. All of the results of FIGS. 4–8 represent actual events.

Figure 2:
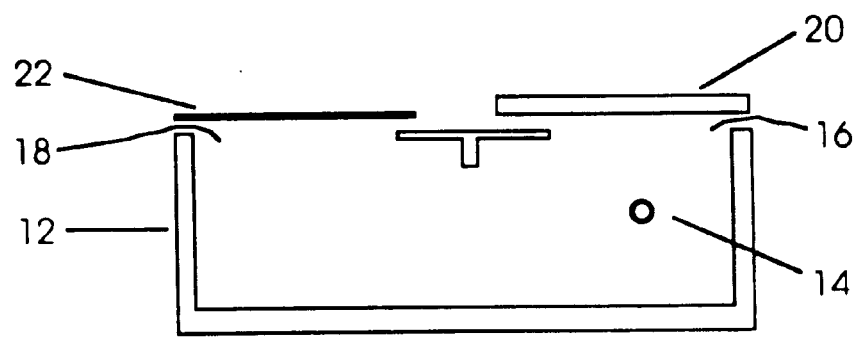
FIG. 2 is a top plan view of the spark discharge chamber of the apparatus of FIG. 1.
Figure 2:
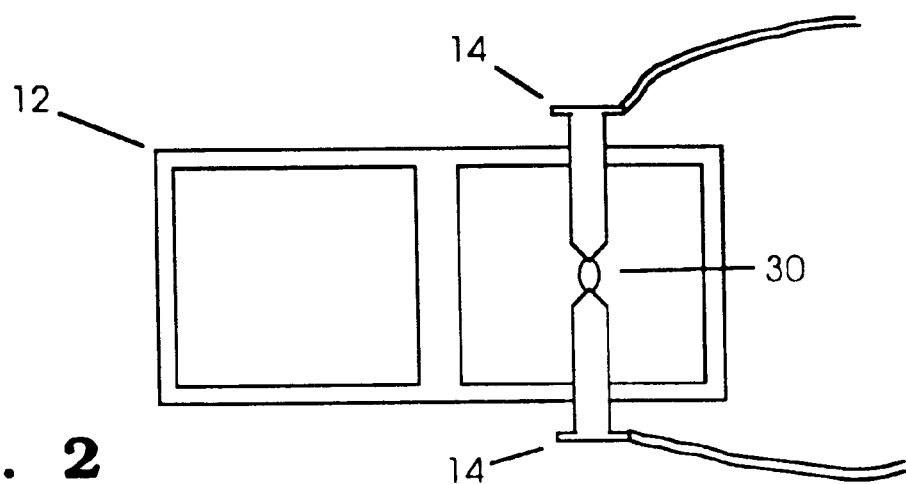

For most of the shoots recovered for the plant transformation process using the apparatus of FIGS. 1 and 2, no expression of the GUS gene in the stem section was found. Of those shoots in which expression in the stem segment was found, and classified in one of the categories as described above, a number of shoots of each category were either induced to root or were grafted onto healthy root stock and cultivated further into plantlets. When the plantlets developed either two or three trifoliate leaves, one or more leaflets from the first trifoliate leaf was harvested from each of the plants and the trifoliate leaflet itself was assayed for activity for the GUS enzyme. Thus new phenotypes could be identified which could be correlated to the phenotypes from the classification on the original stem of the primary regenerate shoot. A number of the plants were found only to express the GUS enzyme in epidermal trichomes and/or hairs either throughout the leaflet or only in certain areas within the leaflet. Other plants were found to express GUS activity only in mesophyll cells or stomata, and the activity in these tissues could extend throughout the leaflets or be confined to one or more specific areas within the leaflet. In other cases, the enzyme activity would be found to be localized in the mid-rib or to extend in varying degrees to one or both sides of the mid-rib in sectors of the leaflet. Examples were even found in which the GUS activity extended from the mid-rib to the perimeter only on one-half of the leaf. Again, the most optimal phenotype observed was that in which the blue color was not either localized into a sector or confined to the epidermis.

Upon further development, a third assay was developed based on petiole and mid-rib sections on a trifoliate leaf higher up the regenerating plant. It was found that if this last assay were not performed, certain non-germ line transformation events would be allowed to go to seed, since certain transformation events seem to give rise to plants in which the transformed tissues only extended a finite length up the stem of the regenerating plant. It became a not uncommon observation to observe GUS activity only in the first trifoliate leaf and not in certain other trifoliates further up the plant. It was, however, the general observation that the majority of plants which had GUS activity in the third or fourth trifoliate leaves would exhibit the same activity in all or most of the leaves of the plants.

The use of these three indicia led to the observation that the transformation process could be optimized to the total overall labor involved if only the plants which were characterized as "B", "P*" or some combination of P and c or C, during the assay of the stem segment, were fully regenerated and allowed to propagate into R1 plants. Even plants which are characterized as B, however, would not prove to have germ line transformation events if the expression of the GUS gene was not also found in the first trifoliate leaf and also in the petiole mid-rib assay in the mature leaf. The best use of the second and third indicia of transformation events were used as negatives, that is to say, plants which failed to properly exhibit the GUS activity at these stages could also be discarded, since the likelihood that such plants would yield germ line transformation events was found to be relatively minimal. Of plants which had been classified as B during the stem segment, and which showed major GUS activity in the pith or pith and cortex during the assay of the petiole and mid-rib sections of the third or fourth trifoliate stage, all plants had activity which was later determined to involve germ line transformation events as evidenced by the recovery of progeny plants which were clonal and expressing the GUS gene. All plants which were classified in any other of the categories described above exhibited a dramatically lower frequency of germ line transformation events, although such events did occur with other classes of tissues. For example, two plants out of 363 which showed activity only in their epidermis at the stem segment stage also gave rise to transformed progeny. However, the likelihood of any transformation events from any other categories of plants was thus so low as to justify, on a practical basis, discarding all but the plants designated above during the stem segment and further to sexually propagate those plants categorized likely to lead to germ line transformation which both exhibited GUS activity at the first trifoliate stage and also showed major pith and cortex involvement during the assay of the petiole and mid-rib of the mature leaf of the plant.

An excess of one-third of the plants classified as "B" would give rise to germ line transformation events. By contrast, plants categorized in other categories during the stem segment as they were found to have a dramatically lower likelihood of germ line transformation event. For example, a plant that is classified as c/p*, the likelihood of a germ line transformation event was less than 10% while for plants showing activity in greater than half their cortex, and classified C, the ratio of transformation events was on the order of 2%. Of plants which had major cortex and pith activity, designated C/P, of which only eight plants were tested, two yielded germ line transformation events. Of six plants which showed activity in less than 50% of the pith, one germ line transformation event was recovered. Thus the exact classifications that are regenerated may depend on a cost analysis of the cost of regeneration of shoots into plants and seeds as compared to the cost of generating more putatively transformed shoots.

EXAMPLES

The target tissues used in the soybean transformation procedures described herein were the excised embryonic axes from immature and mature soybean seeds of elite lines of soybean. The axes were excised from the seeds and plated on target plates on agar. The methodology for excising the seeds and performing the transformation experiment is described in detail in McCabe et al., *Bio/Technology*, 6:923–926 (1988). The apparatus used in the transformation experiments was the apparatus of FIGS. 1 and 2.

After the transformation event was conducted, in excess of 5,000 shoots were recovered, and subject to a stem segment assay. In performing the stem segment assay, the shoots were allowed to reach a length of approximately 2 centimeters before they were severed from the underlying tissue. At the time of severing, a 2 to 4 millimeter section of the base of the shoot was cut off, and assayed for GUS activity. Of the 757 stem segments assayed which showed GUS activity, the plants were categorized on the basis of the kind of activity which was observed in the stem by the categorization system described above, i.e., either B, C/P*, C, C/P, p, c or e. The distribution of the plants as classified can be seen in Table I.

TABLE I

Germ Line Event Frequency

| Stem Segment Assay Classification | Number of Plants | Number expressing in first leaf | Number expressing in mature leaf |
| --- | --- | --- | --- |
| B | 30 | 27 | 13 |
| C/P* | 13 | 5 | 1 |
| C | 45 | 20 | 1 |
| C/P | 8 | 4 | 2 |
| p | 6 | 1 | 1 |
| c | 292 | 9 | 1 |
| e | 363 | 7 | 1 |

All of the plants for whom the stem segment assay was positive to any degree were then either grafted or rooted to create plantlets. The first trifoliate leaf from each of the plantlets was assayed for GUS activity. The results of that assay are indicated by the third column in Table I. All plants which continued to have GUS activity in the first trifoliate leaf were then propagated into plants containing multiple leaves, and mature third or fourth trifoliate level leaves were harvested from the plants and the petiole and mid-rib sections were taken through that leaf and were fixed and assayed for GUS activity. The results of those assays are indicated in the fourth column in Table I. All plants indicated in the fourth column were found to have experienced a germ line transformation event.

The fourth column in Table I indicates those plants which had activity in the pith or pith and cortex of the third or fourth stage trifoliate leaf. All of the plants which had GUS activity were allowed to self-pollinate and reproduce progeny. Analysis of the progeny was then done for GUS activity. It was determined that all of the plants which were indicated in column 4 of this chart to have activity in the pith or pith and cortex of the third or fourth trifoliate leaf stage were found to involve germ line transformation events as indicated by the recovery of progeny plants which expressed the GUS gene.

Of plants which failed to have pith or pith and cortex activity in the third or fourth stage trifoliate leaf, the results were more mixed. Of plants which had been designated B by the stem segment assay, during the assay of the third or fourth trifoliate leaf, 8 of the plants only showed activity in the epidermis while 6 were found to be completely negative in GUS assay. Two of the plants which showed only activity in their epidermis gave rise to transformed progeny. Thus the indication of classification as B is not a predictor alone and of itself of a germ line transformation event. The classification of B thus indicates a likelihood of a high level of recovery of germ line transformation, but cannot be considered alone a highly confident predictor of germ line transformation event in the absence of pith or pith and cortex involvement in the third or fourth trifoliate leaf of the soybean plant.

For the plants for which the stem segment assay caused categorization in another category, the results also gave rise to germ line transformation events, although at a lower frequency. Of the 13 plants characterized as C/P*, 5 plants were recovered which seemed to express GUS throughout their tissues, but only 1 of the plants proved to be a germ line transformation event. Of the 45 plants showing activity in excess of 50% of their cortex, and designated C, 20 GUS expressing plants were found only 1 of which was found to be a germ line transformation event. Of the 8 plants categorized as C/P by virtue of activity in excess of 50% of their cortex, 4 plants were recovered which expressed GUS in their leaves which yielded only 2 plants in which a germ line transformation event was found. Of the 6 plants which showed activity in less than 50% of their pith, a single germ line transformation event was found. Of the 292 R0 plants which showed minor activity in the cortex, 9 plants were recovered which expressed GUS in their leaves and 1 germ line transformation event was recovered. Of 363 R0 plants which showed activity in the epidermal layer only, 7 plants were recovered which seemed to express the GUS in their leaves and only 1 event proved to be a germ line transformation related event.

Based on the data presented in Table I, and related experiments, it was determined that of the soybean plants subjected to the particle-mediated transformation process described herein, between 10 and 15% of the recovered shoots exhibit some form of expression of the GUS gene during the stem segment assay. Of all of the shoots which are the subject of the procedure the percentage which were found to be germ line transformed will ultimately be in the range of 0.2 to 0.5% of the regenerated shoots. Thus by performing the stem segment assay, the number of plants which need to be carried through the regeneration process can be reduced by a factor of 85 to 90%. Then, since it has been found that the highest concentration of germ line transformation events occurs for segments which are categorized as B, C/P*, C, or C/P, all other plants falling in all other categories during the stem segment assay could be discarded on the grounds of low likelihood of finding a germ line transformation event. Since these plants categorize approximately 15% of the total stem segments which exhibit GUS activity at all, again this allows a discard of approximately 85% of the recovered plants so that the efforts for regeneration can be concentrated on the remaining 15% which will show a high likelihood of germ line transformation events. In this way approximately 2 to 2.5% of the shoots recovered from the transformation process need ultimately be propagated, thus saving 97 to 98% of the labor and effort involved in the plant propagation and progeny testing process. Of the 2% which are regenerated through the transformation process, between 10 and 25% of the plants have been found, by assay of the progeny to GUS activity, to have undergone a germ line transformation yielding progeny which are stably transformed and inheritably possess the inserted foreign DNA.

What is claimed is:

1. A method of creating germ line transformed plants comprising the steps of:

(a) preparing an exogenous genetic construction for insertion into plants, the exogenous genetic construction including expression constructs for both a marker gene and a gene of interest, both of the marker gene and the gene of interest expression constructs including a coding sequence and flanking regulatory sequences effective in cells to produce a gene product coded by the coding sequences in the cells of the plants, the flanking regulatory sequences of the expression construct for the marker gene including a promoter effective to express the coding sequence of the marker gene in cells of a plant;

(b) coating copies of the exogenous genetic construction onto carrier particles of biologically inert material, the carrier particles being small in size relative to the size of the cells;

(c) accelerating the coated particles into the cells of a tissue from which shoots may be regenerated;

(d) regenerating shoots from the tissue;

(e) severing a segment of each of the shoots;

(f) assaying the segments for the expression of the gene product of the marker gene to determine if and where each shoot is expressing the marker gene in its tissues;

(g) classifying the stem segments based upon the extent of expression of the marker gene in the severed segments;

(h) regenerating those shoots, the segments of which expressed the gene product of the marker gene in a majority of its cells, into whole sexually mature plants;

(i) sexually propagating the whole plants to create progeny plants; and (j) assaying for the expression of the gene product of the marker gene in the progeny plants to indicate the germ line insertion of the gene of interest into the progeny plants.

* * * * *